United States Patent
Inoue et al.

(10) Patent No.: US 11,553,949 B2
(45) Date of Patent: Jan. 17, 2023

(54) FEMORAL FRACTURE FIXATION DEVICE WITH POSTERIOR SUPPORT PORTION

(71) Applicant: Biomet Manufacturing, LLC, Warsaw, IN (US)

(72) Inventors: Hisayoshi Inoue, Miyagi (JP); Koichi Kanekasu, Takaoka (JP); Takashî Maehara, Okayama (JP)

(73) Assignee: Biomet Manufacturing, LLC, Warsaw, IN (US)

( * ) Notice: Subject to any disclaimer, the term of this patent is extended or adjusted under 35 U.S.C. 154(b) by 444 days.

(21) Appl. No.: 16/630,712

(22) PCT Filed: Jul. 18, 2018

(86) PCT No.: PCT/US2018/042694
§ 371 (c)(1),
(2) Date: Jan. 13, 2020

(87) PCT Pub. No.: WO2019/018528
PCT Pub. Date: Jan. 24, 2019

(65) Prior Publication Data
US 2021/0077163 A1    Mar. 18, 2021

Related U.S. Application Data

(60) Provisional application No. 62/535,545, filed on Jul. 21, 2017.

(51) Int. Cl.
*A61B 17/74*    (2006.01)
(52) U.S. Cl.
CPC .......... *A61B 17/744* (2013.01); *A61B 17/746* (2013.01)

(58) Field of Classification Search
CPC ...... A61B 17/74; A61B 17/744; A61B 17/746
See application file for complete search history.

(56) References Cited

U.S. PATENT DOCUMENTS 7,731,718 B2 *  6/2010  Schwammberger ... A61B 17/80
                                                     606/71
8,177,819 B2    5/2012  Huebner et al.
(Continued)

FOREIGN PATENT DOCUMENTS

| CN | 102247205 B | 8/2012 |
| CN | 103610494   | 3/2014 |

(Continued)

OTHER PUBLICATIONS

"International Application Serial No. PCT US2018 042694, International Preliminary Report on Patentability dated Jan. 30, 2020", 9 pages.

(Continued)

*Primary Examiner* — Anu Ramana
(74) *Attorney, Agent, or Firm* — Schwegman Lundberg & Woessner, P.A.

(57) ABSTRACT

Described is a femur fracture fixation device for treating a fractured, proximal end portion of a femur. The femur fracture fixation device comprises: an intramedullary nail; an extramedullary plate, including a main body portion for attachment to a lateral surface of the femur, and a posterior support portion extending from the main body portion for attachment to a posterior surface of the greater trochanter region of the femur; and a bone fastener, configured for insertion through an opening of the main body portion of the extramedullary plate, through an opening of the intramedullary nail, and into the head portion of the femur.

12 Claims, 9 Drawing Sheets

(56) References Cited

U.S. PATENT DOCUMENTS

| | | |
|---|---|---|
| 8,734,448 B2 | 5/2014 | Thakkar |
| 8,894,693 B2 | 11/2014 | Petit et al. |
| 9,339,313 B1 | 5/2016 | Powlan |
| 9,387,020 B2 | 7/2016 | Geissler et al. |
| 9,463,054 B2 | 10/2016 | Mueckter |
| 2004/0210220 A1 | 10/2004 | Tornier |
| 2005/0240187 A1 | 10/2005 | Huebner et al. |
| 2007/0123880 A1 | 5/2007 | Medoff |
| 2008/0119895 A1* | 5/2008 | Manceau ........... A61B 17/8047 606/301 |
| 2012/0226323 A1 | 9/2012 | Gonzalez-hernandez |
| 2014/0378973 A1 | 12/2014 | Mueckter |

FOREIGN PATENT DOCUMENTS

| | | |
|---|---|---|
| CN | 105125274 | 12/2015 |
| JP | 2016129625 A | 7/2016 |
| JP | 2020527984 | 9/2020 |
| WO | WO-2019018528 A1 | 1/2019 |

OTHER PUBLICATIONS

"Japanese Application Serial No. 2020-502668, Notification of Reasons for Refusal dated Apr. 20, 2021", with English translation, 6 pages.

"Japanese Application Serial No. 2020-502668, Response filed Jul. 14, 2021 to Notification of Reasons for Refusal dated Apr. 20, 2021", with English claims, 16 pages.

"International Application Serial No. PCT/US2018/042694, International Search Report dated Oct. 26, 2018", 5 pgs.

"International Application Serial No. PCT/US2018/042694, Written Opinion dated Oct. 26, 2018", 7 pgs.

\* cited by examiner

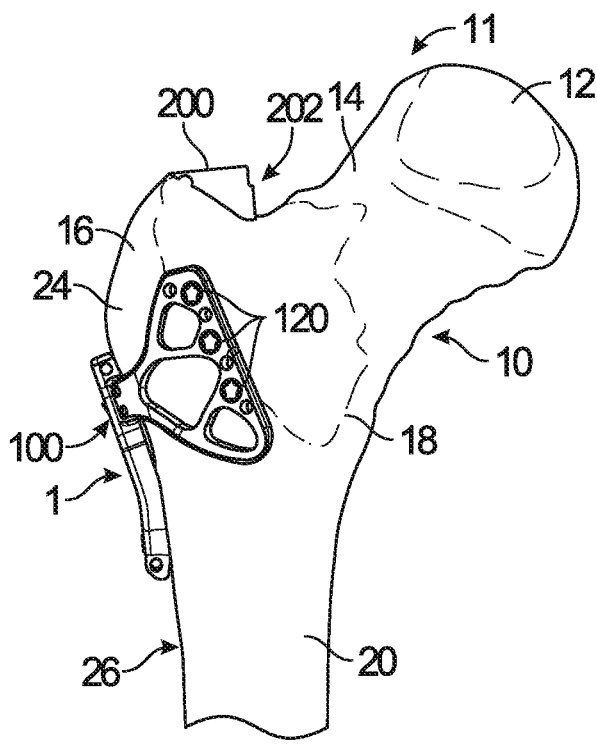
FIG. 3
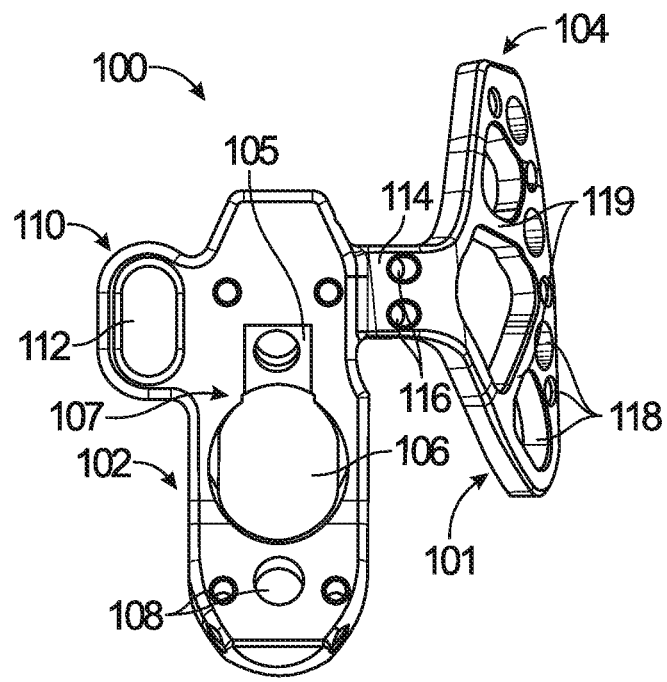 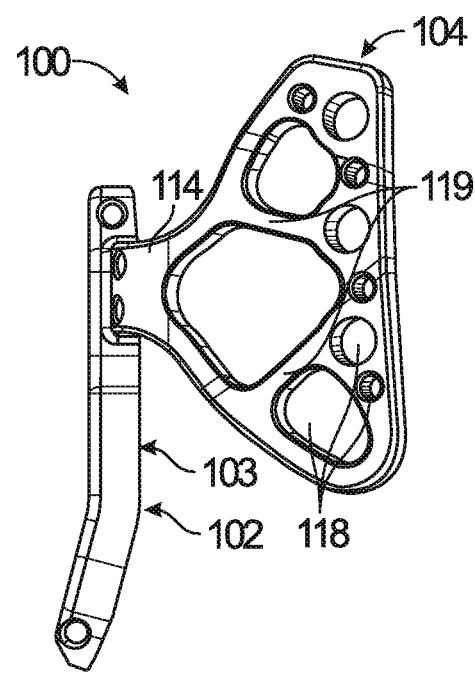
FIG. 4 FIG. 5

FEMORAL FRACTURE FIXATION DEVICE WITH POSTERIOR SUPPORT PORTION

CLAIM OF PRIORITY

This application is a U.S. National Stage Application under 35 U.S.C. 371 from International Application Serial No. PCT/US2018/042694, filed on Jul. 18, 2018, and published as WO 2019/01852.8 Al on Jan. 24, 2019, which claims the benefit of U.S. Provisional Patent Application Ser. No. 62/535,545, filed on Jul. 21, 2017, the benefit of priority of which is claimed hereby, and which is incorporated by reference herein in its entirety.

FIELD

The present subject matter relates generally to orthopedic implants. In particular, the present disclosure relates to an orthopedic implant device used to repair fractures of the proximal femur.

BACKGROUND

In the realm of orthopedic surgery, it is known to use implants to fix the position of bones. In this way, bones can be reconstructed, and malformations or other injuries corrected. There exists a wide variety of situations in which it is desirable to fixate adjacent bone pieces or segments to promote healing of a fracture.

Trochanteric and subtrochanteric femur fractures are currently treated with an intramedullary nail or rod that can be inserted and fixed within a femur having a proximal end fracture or fractures. Typically, during a minimally invasive procedure, the intramedullary nail is inserted through a proximal end of the femur and into a medullary cavity in the femur. One or more cortical screws can then be inserted through cortical bone of one side of the femur, through a bore extending through the intramedullary nail and into cortical bone of a second side of the femur.

A screw, sometimes called a "lag screw," can also be inserted through cortical bone and a bore in a proximal end portion of the intramedullary nail. Such a lag screw can include a distal end portion that can be inserted into a head portion of the femur. The distal end portion of the lag screw can engage trabecular or cancellous bone within the head portion of the femur. After the lag screw has engaged the head portion, the head portion can be pulled by the lag screw toward a neck portion and a shaft portion of the femur to rejoin the head portion with the femur at a fracture in the region of the femur known as a greater trochanter, for example.

OVERVIEW

The present inventors have recognized the need for improved orthopedic implant devices used to stabilize fractures of a proximal end of a long bone, such as a femur. The disclosure provides an orthopedic implant device intended to be used generally with long bones, such as the femur. The disclosure also provides an insertion tool for inserting a component of the orthopedic implant device.

Particularly, the disclosure provides a femoral fracture fixation device that can include an extramedullary plate including a posterior support portion that can be attached to a femur on a posterior side. In addition to including the extramedullary plate, the device can include an intramedullary nail and a bone fastener in the head of the femur in order to stabilize or fix fragments of a fractured proximal end of the femur. The posterior support portion, in particular, can provide additional stabilization of the fractured, proximal end of the femur, possibly in a region of a greater trochanter. A benefit of using the posterior support portion can include allowing for improved fixation of the femoral fracture fixation device to the femur as well as improved stabilization of fractured bone segments of the femur. Other benefits of including the posterior support portion can include a reduction in post-operative complications and improved healing of the femur.

The disclosure also provides an insertion tool for insertion of the bone fastener of the femoral fracture fixation device. The bone fastener insertion tool can be attached temporarily to the extramedullary plate in order to insert the bone fastener through the extramedullary plate, through the intramedullary nail and into the femur. A benefit of using the disclosed bone fastener insertion tool is that the tool need only be attached to the extramedullary plate in order to insert the bone fastener properly. Other such insertion tools require additional attachments, such as to the intramedullary nail on a proximal end thereof. The bone fastener insertion tool, therefore, can simplify and speed up insertion of the bone fastener during implantation of the disclosed femoral fracture fixation device.

These and other examples and features of the present devices, systems and methods will be set forth in part in the following Detailed Description. This Overview is intended to provide non-limiting examples of the present subject matter—it is not intended to provide an exclusive or exhaustive explanation. The Detailed Description below is included to provide further information about the present apparatuses and methods.

BRIEF DESCRIPTION OF THE DRAWINGS

In the drawings, which are not necessarily drawn to scale, like numerals can describe similar components in different views. The drawings illustrate generally, by way of example, but not by way of limitation, various examples discussed in the present disclosure.

FIG. 3 shows a side view of the femoral fracture fixation device and the femur bone shown in FIGS. 1-2, in accordance with one example of the present disclosure.

FIG. 4 shows a front view of an extramedullary plate of the femoral fracture fixation device shown in FIGS. 1-3, in accordance with one example of the present disclosure.

FIG. 5 shows a side view of the extramedullary plate shown in FIG. 4, in accordance with one example of the present disclosure.

the present disclosure.

Figure 17A:
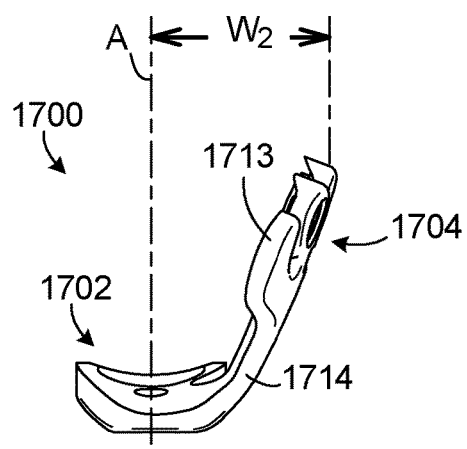

FIG. 17A shows a top view of an extramedullary plate, in accordance with one example of the present disclosure.

Figure 17B:
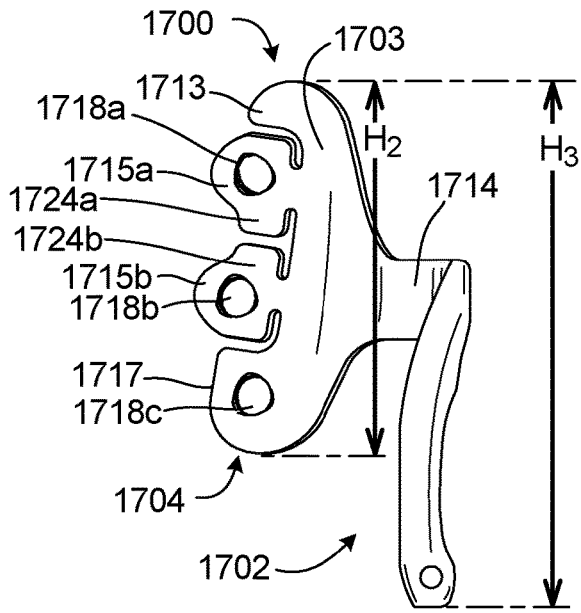

FIG. 17B shows a side view of an extramedullary plate, in accordance with one example of the present disclosure.

Figure 17C:
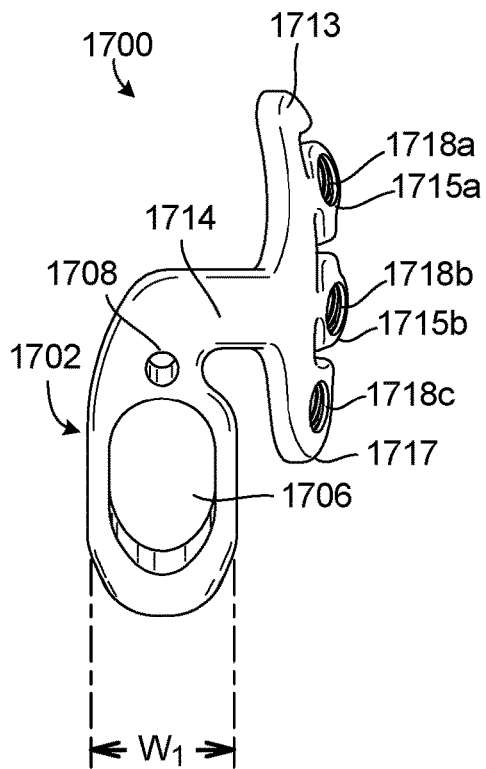

FIG. 17C shows a front view of an extramedullary plate, in accordance with one example of the present disclosure.

Figure 17D:
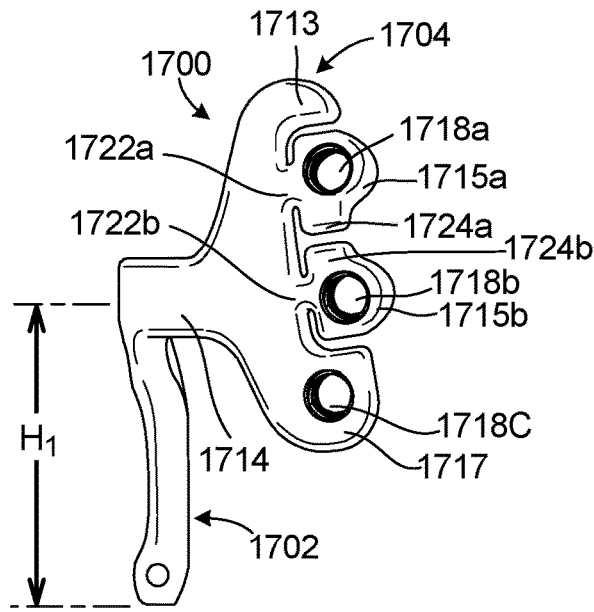

FIG. 17D shows a side view of an extramedullary plate, in accordance with one example of the present disclosure.

DETAILED DESCRIPTION

With reference to the human body and components of the device described herein, which are intended to be implanted in the human body, the terms "proximal" and "distal" are defined in reference to the location at which a limb is connected to the torso, with the term "proximal" being the end of the limb, bone or plate closer to the torso, and the term "distal" being the end of the limb, bone or plate further from the torso. In addition, the term "lower" and "upper" in reference to plate surfaces are designations in which the lower surface (or "bone contacting surface") is that surface closer to or seating on the bone and the upper surface is that surface opposite the lower surface.

The present disclosure relates to an orthopedic implant device. In particular, the orthopedic implant device shown and described herein is a femoral fracture fixation device suitable for fixation of a fractured, proximal end of a femur. However, it is contemplated that the orthopedic implant device described herein can be varied in order to be used with other long bones.

Figure 1:
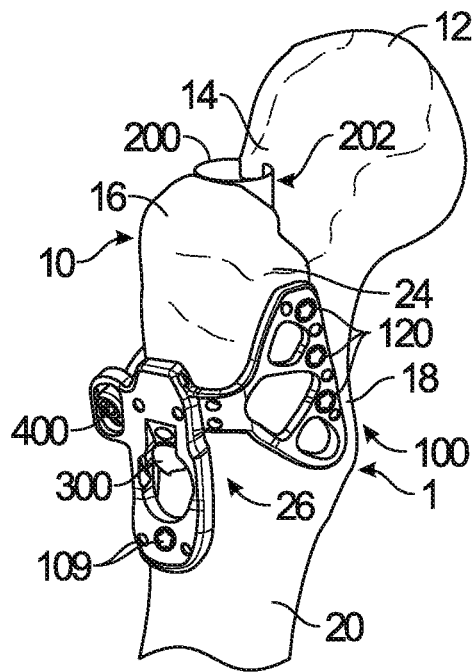
FIG. 1 shows a perspective view of a femoral fracture fixation device, in accordance with an example of the present disclosure, operatively mounted to a femur bone, only a proximal portion of which is shown.

Referring to FIG. 1, there is shown, in a perspective view, a femoral fracture fixation device 1 in accordance with an example of the present disclosure. The femoral fracture fixation device 1 is shown, by way of example, mounted to a femur generally indicated by reference numeral 10. The femoral fracture fixation device 1 can be attached to femur 10 to stabilize fractured segments of the bone in order to allow the femur 10 to heal.

Figure 2:
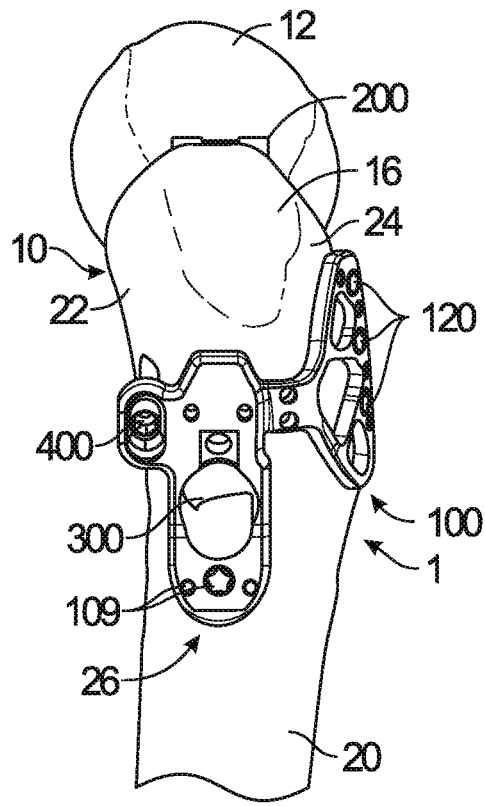
FIG. 2 shows a front view of the femoral fracture fixation device and the femur bone shown in FIG. 1, in accordance with one example of the present disclosure.

The femoral fracture fixation device 1 shown can include an extramedullary plate 100, an intramedullary nail 200, a bone fastener 300, and an anterior connecting fastener 400. The intramedullary nail 200 can be inserted into a marrow or medullary cavity 28 of the femur 10. FIG. 2 shows a front view, and FIG. 3 shows a side view, of the femoral fracture fixation device 1 and the femur 10 of FIG. 1. It should, however, be understood that the femoral fracture fixation device 1 is shown mounted to/in the femur 10 by way of example and that the orthopedic implant system can be alternatively used for fixating or securing bone segments located at other anatomical regions without departing from the present disclosure.

FIGS. 1-3 show a proximal end portion of the femur 10 that can include one or more fractures or segments. The proximal end portion can include a femur head 12, a femur neck 14, a greater trochanter 16 and a lesser trochanter 18. The femur neck 14 connects the femur head 12 to the femur shaft 20. The greater trochanter 16 is a substantially large, somewhat rectangular projection from the junction of the femur neck 14 and the femur shaft 20. The greater trochanter 16 includes an anterior surface 22 and a posterior surface 24 that are oriented toward the anterior and posterior sides of a patient's body, respectively.

Referring to FIGS. 4-5, there is shown in greater detail some of the exemplary features of the extramedullary plate 100 of the femoral fracture fixation device 1 shown in FIGS. 1-3. In general, the extramedullary plate 100 can be contoured so as to follow the general shape of a lateral surface 26 of the femur 10 near a proximal end 11 of the femur 10. The extramedullary plate 100 can also conform to a surface of the femur 10 extending at least toward a posterior side 24 of the femur 10, near a region of the greater trochanter 16. It should be appreciated that in order for the extramedullary plate 100 to be fitted across a range of bone sizes, shapes and types, the shapes and sizes can vary across a range of extramedullary plates.

The extramedullary plate 100, an example of which is shown in detail in FIGS. 4-5, can include a main body portion 102 that can have a bone contacting surface 103 to be connected to the lateral surface 26 of the femur 10 (lateral surface 26 shown in FIGS. 1-3) and a posterior support portion 104 that can be connected to the posterior side or surface 24 of the femur 10 in the region of the greater trochanter 16. The main body portion 102 of the extramedullary plate 100 can include at least one opening or through hole 106 through which the bone fastener 300 (shown in FIGS. 1-2) can extend. The area of the main body portion 102, indicated by 107 (FIG. 4), including the through hole 106 and an upper, squared portion 105, can be configured for connection to a bone fastener insertion assembly 500 for insertion of the bone fastener 300 (FIGS. 8-9) into the femur 10, which will be discussed in more detail below. The bone fastener 300, once inserted through the extramedullary plate 100 can extend into and through the femur 10 and an intramedullary nail 200 (while in place in the medullary cavity 28), which will also be discussed in more detail below.

The main body portion 102 of the extramedullary plate 100 can also include additional openings 108, besides opening 106, through which additional fasteners 109 (some examples of which are indicated in FIGS. 1-2) can extend and attach the main body portion 102 to the femur 10. The openings 108 can be threaded or non-threaded and can have various sizes and shapes. The fasteners 109 can be bone screws, for example, which can attach the extramedullary plate 100 at or near the lateral surface 26 of the proximal end of the femur 10. Other suitable fasteners of various types, sizes and shapes are contemplated by the present disclosure.

The posterior support portion 104 of the extramedullary plate 100 can be substantially wing-shaped, as shown, or can otherwise include a shape that extends posteriorly from the main body portion 102 in the region of the greater trochanter 16 of the femur 10. A bone contacting surface 101 (see FIG. 4) of the posterior support portion 104 can have an arcuate shape capable of conforming to an arcuate bone surface, the bone contacting surface 101 forming a concave portion of the arcuate shape.

The posterior support portion 104 can be attached to the main body portion 102 by a connection portion 114. The connection portion 114 can be narrower in width than both the main body portion 102 and the posterior support portion 104, as shown, or can be any suitable width. The connection portion 114 can include, as shown, one or more openings 116 (two such openings 116 are shown) through which one or more bone screws or fastening devices can extend to attach the connection portion 114 to the femur 10.

The posterior support portion 104 can curve around the femur 10 and can flare out in width from the connection portion 114 in the wing-shape shown, for example, and can be shaped and proportioned to fit against the posterior surface 24 of the region of the greater trochanter 16 (as in FIG. 1). Other suitable shapes of posterior support portions, besides the wing-shape, are also contemplated by the disclosure. Also, other sizes, relative to the main body portion 102, other than those shown, are also contemplated by the disclosure.

Figure 6:
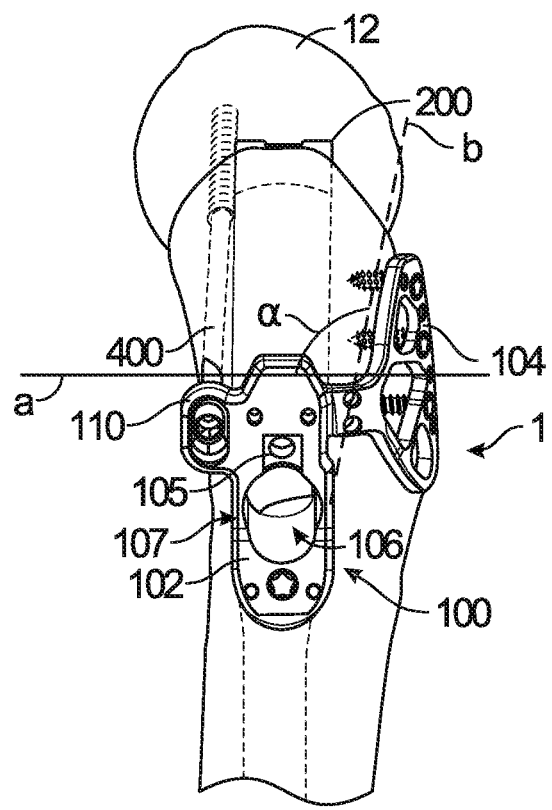
FIG. 6 shows the front view of the femoral fracture fixation device and the femur bone shown in FIG. 2, illustrating certain components in phantom, in accordance with one example of the present disclosure.

The posterior support portion 104 can be arranged such that the bone contacting surface 105 of the posterior support portion 104 is at a suitable angle α from the bone contacting surface 103 of the main body portion 102 that can contact the lateral surface 24 of the femur 10. The angle α (an example of which is shown in FIG. 6, the angle α shown between axes, a and b, that run through the bone contacting surfaces of the main body portion 102 and the posterior support portion 104, respectively) can be chosen in order to allow the posterior support portion 104 to contact the posterior surface 24 of the greater trochanter region, for example, while the main body portion 102 contacts the lateral surface 26 of the femur 10. The angle α at which the bone contacting surface 105 of the posterior support portion 104 can be angled from the bone contacting surface 103 of the main body portion 102 can be in a range of about 10 to about 230 degrees from the bone contacting surface 103 of the main body portion 102. The angle α can be provided by a curvature in the connection portion 114 (as shown in FIGS. 4-5) of the extramedullary plate 100, for example. Alternatively, a portion (not shown) of the posterior support portion 104 can be curved resulting in the remainder of the posterior support portion 104 angling away from the main body portion 102, or a portion (not shown) of the main body portion 102 can be curved resulting in curvature in the extramedullary plate 100.

The posterior support portion 104 can include multiple openings 118 having different possible shapes and sizes, some of which can be sized and shaped to accommodate bone screws or other suitable fasteners. The openings 118 can be threaded or non-threaded. Bone screws, such as those indicated by reference numeral 120 in FIGS. 1-3, can extend through such openings 118 and can be used to affix the posterior support portion 104 to the posterior side or surface 24 of the greater trochanter 16. Between the multiple openings 118, there can be struts 119, which can provide support while reducing material weight of the posterior support portion 104.

The extramedullary plate 100 can also include a flange portion 110 that can extend anteriorly from the main body portion 102 when the extramedullary plate is attached to the femur 10, as shown. The flange portion 110 can include an elongated opening 112 that can accommodate the anterior connecting fastener (400 in FIGS. 1-2) that can extend into the femur head 12 (FIGS. 1-2). The anterior connecting fastener 400 can be a long bone screw, for example. The anterior connecting fastener 400 can extend through the flange portion 110 of the extramedullary plate 100 and a distal portion thereof can extend into the femur 10. A portion of the anterior connecting fastener 400 can extend therebetween and be located outside of the femur 10. Alternatively, more or less of the anterior connecting fastener 400, from that shown in the figures, can be located within the femur 10. The flange portion 110 and the anterior connecting fastener 400 together can serve to further stabilize the femoral fracture fixation device 1 to the femur 10.

The extramedullary plate 100 can have a generally uniform thickness of between about 2 mm and about 15 mm, for example. The main body portion 102 can, alternatively, have an increased thickness from the remainder of the extramedullary plate 100. Any suitable thickness of the extramedullary plate 100 is contemplated and within the scope of this disclosure The extramedullary plate 100, as well as the fasteners used therewith, can be faulted of titanium, stainless steel, cobalt chrome, plastic such as polyetheretherketone (PEEK), polyethylene, ultra high molecular weight polyethylene (UHMWPE), or a carbon composite-resorbable polylactic acid (PLA), polyglycolic acid (PGA), combinations or alloys of such materials or any other appropriate material that has sufficient strength to be secured to and hold bone, while also having sufficient biocompatibility to be implanted into a body. Although the above list of materials includes many typical materials out of which bone plates and bone screws are generally made, it should be understood that bone plates and bone screws or fasteners comprised of any appropriate, biocompatible material are within the scope of this disclosure.

Figure 7:
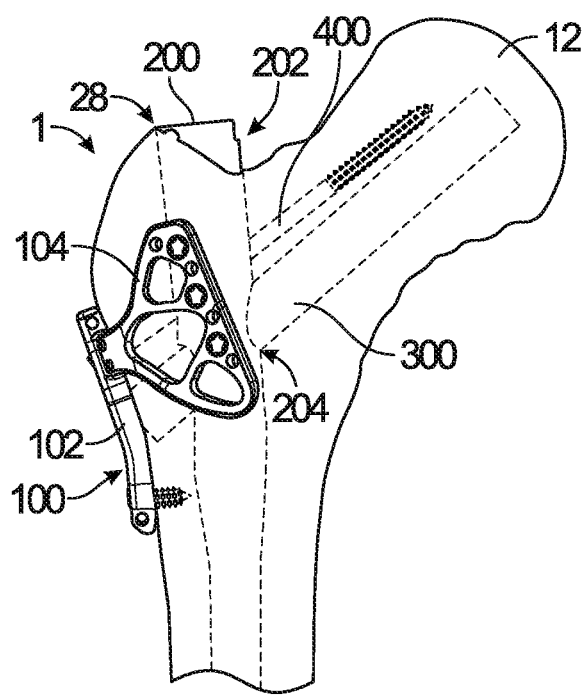
FIG. 7 shows the side view of the femoral fracture fixation device and the femur bone shown in FIG. 3, illustrating certain components in phantom, in accordance with one example of the present disclosure.

The intramedullary nail 200 of the femoral fracture fixation device 1 can be inserted into the medullary cavity 28 of the femur 10. FIGS. 6-7 show how the intramedullary nail 200 (a proximal portion thereof only is shown) can be inserted into the medullary cavity 28. A tool (not shown) may be used to form the medullary cavity 28, or enlarge the medullary cavity 28 to accommodate the intramedullary nail 200. The intramedullary nail 200 can be one commonly known in the art, and comprised of any suitable biocompatible material, such as those listed above with regard to the extramedullary plate 100. The intramedullary nail 200 can be cannulated along its length and can comprise different portions, which can include a proximal, thigh end portion, a larger cross-section portion and a knee end portion (with only the proximal, thigh end portion thereof shown in FIGS. 6-7). The cross-sectional and wall thickness of the intramedullary nail 200 can reduce gradually from the thigh end to the knee end in order to match the shape of the intramedullary nail 200 with the shape of the medullary cavity 28, which generally tapers.

The bone fastener 300, most visible in FIG. 7, can be inserted through opening 106 in extramedullary plate 100.

An angle, shape and configuration of the opening 106 can allow the bone fastener 300 to be directed through the opening 116 and into the femur 10 at a correct angle to allow the bone fastener 300 to be inserted through a corresponding proximal opening or bore 204 (see FIG. 7) in the intramedullary nail 200. The bone fastener 300 can then extend through the proximal opening 204 in the intramedullary nail 200 and into the femur head 12.

The bone fastener 300, as shown in FIG. 7, can be tubular or cylindrical in shape and can be non-threaded. However, the bone fastener 300 can alternatively have a reduced diameter, like that of a bone screw, and/or can have threading on a distal end, for example. Any suitable bone fastener is contemplated by the present disclosure in order to attach the extramedullary plate 100 to the intramedullary nail 200 and the femur 10.

The present disclosure includes a method of implanting the femoral fracture fixation device 1. The femoral fracture device 1, or an alternative embodiment, can be inserted into a patient using a known, closed, intramedullary surgical technique which requires minimal exposure of the femur. Image intensification equipment can be employed to guide the surgeon during the procedure.

Generally, the medullary cavity 28 of the femur 10 can be first reamed with an appropriate known reaming tool to create or enlarge the medullary cavity 28 for insertion of the intramedullary nail 200. Progressively larger reaming tools can be inserted into a proximal end of the femur 10, and can be used to increase the diameter of the medullary cavity 28. A guide pin or wire can be inserted into the cavity 28, and then the intramedullary nail 200 can be guided into the medullary cavity 28 of the femur 10.

Next, the extramedullary plate 100 can be attached to the femur 10. Any number of bone screws or fastening devices can be inserted through any of the openings in the extramedullary plate 100 in order to sufficiently attach the extramedullary plate 100 to the femur 10. Fasteners, such as bone screws, can be used in both the main body portion 102 and the posterior support portion 104 in order to fixate the extramedullary plate 100 to the femur 10.

Figure 8:
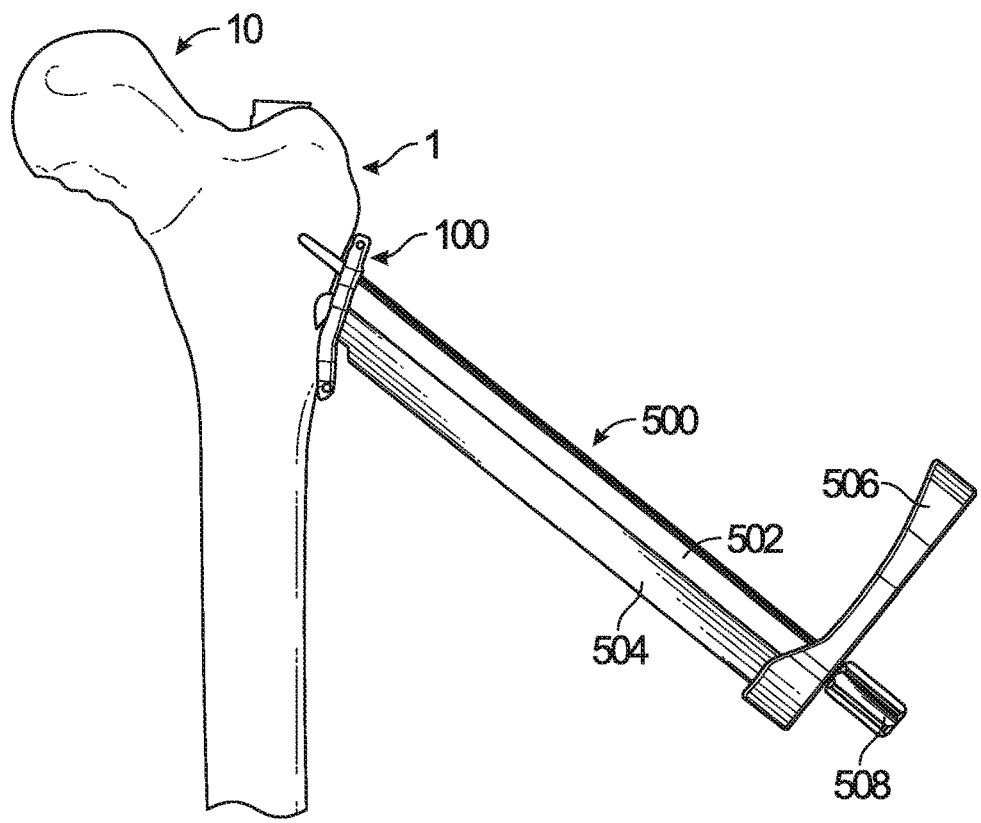
FIG. 8 shows a side view of a bone fastener insertion assembly that can be used with the femoral fracture fixation device shown in FIGS. 1-3, in accordance with one example of the present disclosure.
Figure 9:
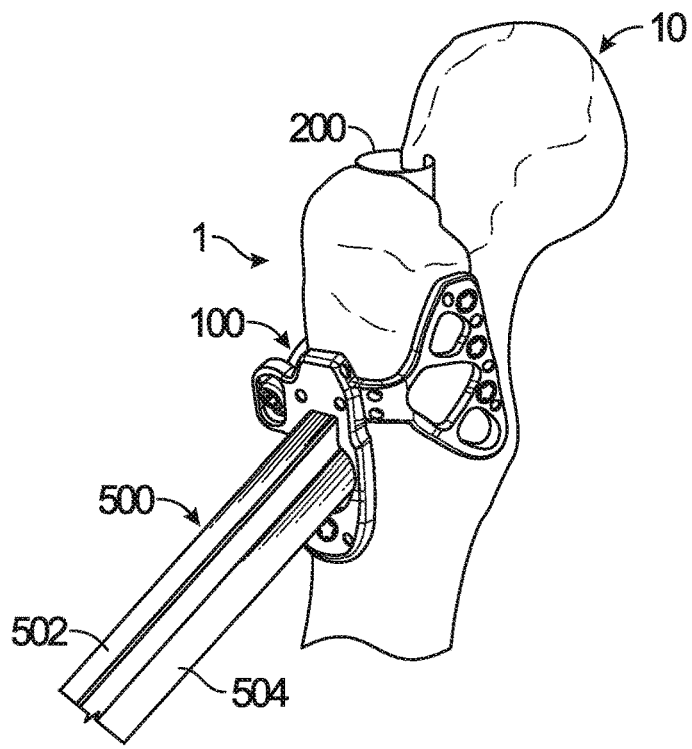
FIG. 9 shows a perspective view of a portion of the bone fastener insertion assembly shown in FIG. 8, in accordance with one example of the present disclosure.

Next, the bone fastener 300 can be inserted through opening 106 in extramedullary plate 100. FIGS. 8-9 show an exemplary bone fastener insertion assembly 500 that can be used with the femoral fracture fixation device 1 in order to implant the bone fastener 300. After the intramedullary nail 200 is inserted, and after the extramedullary plate 100 is attached to the femur 10, the bone fastener 300 can be inserted by the bone fastener insertion assembly 500, for example.

The bone fastener insertion assembly 500 can include a coupling sheath 502, a bone fastener sheath 504 through which the bone fastener 300 can be inserted, and a handle 506. A distal end of the coupling sheath 502 can fit within the area of the extramedullary plate 100 represented by reference numeral 107. The shape of 107 shown represents only one suitable shape, and includes a circular opening 106 and another cut-out area 105 shown with a square-shape and with a smaller opening that is located proximal to the opening 106. The coupling knob 508 can be rotated to temporarily attach and detach a temporary fastener that can attach the coupling sheath 502 to the smaller opening within area 105 and 107 in the extramedullary plate 100. The temporary fastener (not shown) can hold the bone fastener insertion assembly 500 to the extramedullary plate 100 in a correct orientation in order to insert the bone fastener 300 through the extramedullary plate 100 and into the femur 10 and the intramedullary nail 200 as desired.

Once the bone fastener insertion assembly 500 is attached to the extramedullary plate 100, as shown in FIGS. 8-9, a bone fastener 300 can be loaded into bone fastener sheath 504, moved distally, inserted through opening 106 in the extramedullary plate 100, through the opening 204 in the intramedullary nail 200 and into the femur head 12. Optionally, a guide wire can be inserted through the bone fastener sheath 504 before the bone fastener 300 is inserted in order to guide the bone fastener 300 to the correct location (not shown). The bone fastener insertion assembly 500 can then be removed from the extramedullary plate 100.

Figure 10:
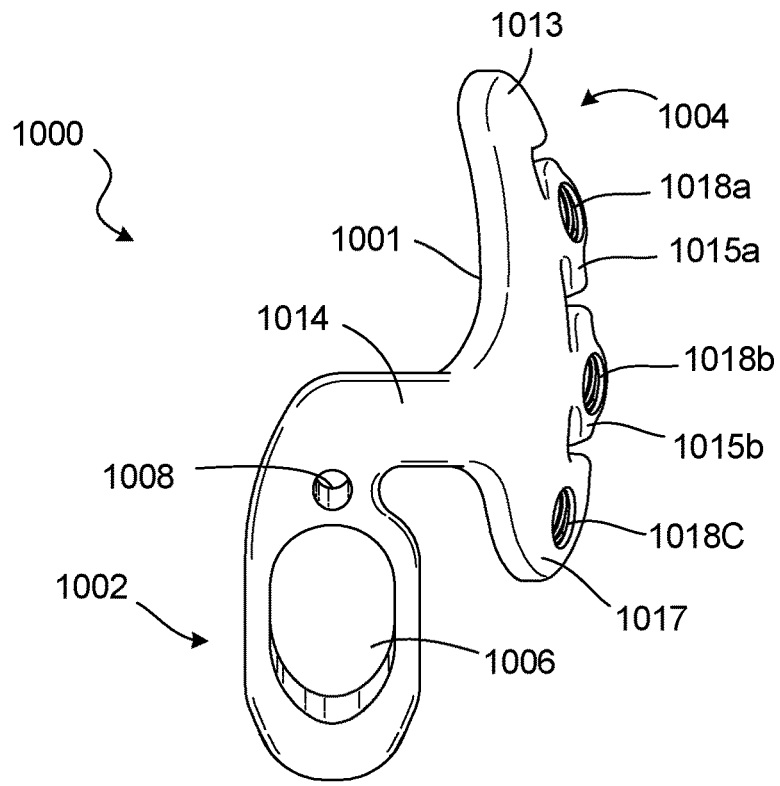
FIG. 10 shows a front view of an extramedullary plate, in accordance with one example of the present disclosure.
Figure 11:
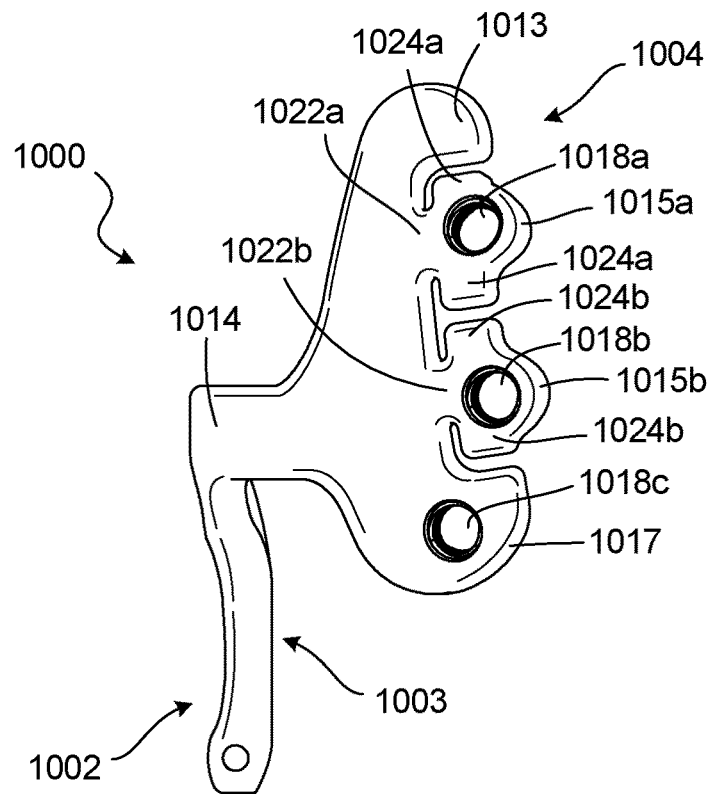
FIG. 11 shows a side view of the extramedullary plate shown in FIG. 10, in accordance with one example of the present disclosure.

FIG. 10 shows a front view of an extramedullary plate 1000, in accordance with one example of the present disclosure. FIG. 11 shows a side view of the extramedullary plate 1000, in accordance with one example of the present disclosure. FIGS. 10 and 11 are discussed below concurrently.

The extramedullary plate 1000 can include a main body portion 1002, a posterior support portion 1004, and a connecting portion 1014. The main body portion 1002 can include a bone contacting surface 1003 (only visible in FIG. 11), a bone anchor opening 1006 (only visible in FIG. 10), and an opening 1008 (only visible in FIG. 10). The posterior support portion 1004 can include a proximal finger 1013, medial fingers 1015a and 1015b, and a distal finger 1017. The medial fingers 1015a and 1015b can include medial openings 1018a and 1018b, respectively, and the distal finger 1017 can include distal opening 1018c.

The main body portion 1002 can be a rigid or semi-rigid member configured to engage and couple to a lateral surface of a femur shaft. The posterior support portion 1004 can also be a rigid or semi-rigid member coupled to the main body portion 1002 by the connecting portion 1014. The connecting portion 1014 can be narrower in width than both the main body portion 1002 and the posterior support portion 1004, as shown, or can be any suitable width. The posterior support portion 1004 can extend posteriorly from the main body portion 1002 and can be configured to couple to a posterior surface of a greater trochanter region of the femur.

The main body portion 1002 can include the bone anchor opening 1006, which can be an opening through the main body portion 1002. The bone anchor opening 1006 can have an oval shape that is symmetrical along one or more axes in some examples and that is non-symmetrical in other examples. The bone anchor opening 1006 can be sized and shaped to receive a bone anchor therethrough, as discussed further below. The main body portion 1002 can also include the opening 1008, which can be another opening through the main body portion 1002. The opening 1008 can be threaded or non-threaded and can be sized and shaped to receive another fastener therethrough.

The proximal finger 1013, the medial fingers 1015a and 1015b, and the distal finger 1017 can be rigid or semi-rigid portions, each extending posteriorly from the posterior support portion 1004. In some examples, the medial fingers 1015a and 1015b and the distal finger 1017 can include the openings 1018a-1018c which can be threaded or non-threaded openings and can be sized and shaped to receive fasteners therethrough. In some examples the proximal finger 1013 can also include an opening and in other examples, fewer of the proximal finger 1013, the medial fingers 1015a and 1015b, and the distal finger 1017 can include openings.

In some examples, the medial fingers 1015a and 1015b can include joints 1022a and 1022b, respectively, which can have a width allowing each of the medial fingers 1015a and 1015b to move relative to the posterior support portion 1004 and relative to each other, as well as relative to the proximal finger 1013 and the distal finger 1017. In operation of some examples, the medial fingers 1015a and 1015b can be articulated or bent to a desired position by a surgeon or physician to interface with a portion of a surface of a femur, as discussed further below. In some examples, the proximal finger 1013 and the distal finger 1017 can include a joint, and in other examples, the proximal finger 1013 and the distal finger 1017 can rigidly cantilever from the proximal support portion 1004.

In some examples, the medial fingers 1015a and 1015b can include tabs 1024a and 1024b, respectively, which can be proximal and distal extensions from the fingers 1015a and 1015b towards adjacent fingers. The tabs 1024a and 1024b can be sized to control movement or deflection of fingers 1015a and 1015b relative to each other by causing contact when a maximum desired deflection is reached.

The extramedullary plate 1000 can have a generally uniform thickness of between about 2 mm and about 15 mm, for example. The main body portion 1002 can, alternatively, have an increased thickness from the remainder of the extramedullary plate 1000. Any suitable thickness of the extramedullary plate 1000 is contemplated and within the scope of this disclosure.

Figure 12:
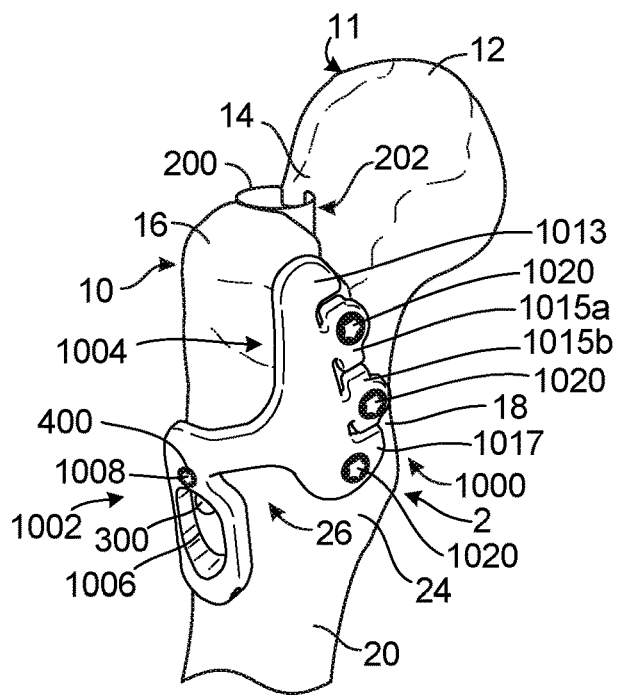
FIG. 12 shows a perspective view of a femoral fracture fixation device operatively mounted to a femur bone, in accordance with one example of the present disclosure.

In some examples, posterior support portion 1004 of the extramedullary plate 1000 can be substantially wing-shaped, as shown, or can otherwise include a shape that extends posteriorly from the main body portion 1002 in the region of the greater trochanter 16 of the femur 10, as shown in FIG. 12. A bone contacting surface 1001 of the posterior support portion 1004 can have an arcuate shape capable of conforming to an arcuate bone surface, the bone contacting surface 1001 forming a concave portion of the arcuate shape.

In some examples, the extramedullary plate 1000, as well as the fasteners used therewith, can be formed of titanium, stainless steel, cobalt chrome, plastic such as polyetheretherketone (PEEK), polyethylene, ultra high molecular weight polyethylene (UHMWPE), or a carbon composite resorbable polylactic acid (PLA), polyglycolic acid (PGA), combinations or alloys of such materials or any other appropriate material that has sufficient strength to be secured to and hold bone, while also having sufficient biocompatibility to be implanted into a body. Although the above list of materials includes many typical materials out of which bone plates and bone screws are generally made, it should be understood that bone plates and bone screws or fasteners comprised of any appropriate, biocompatible material are within the scope of this disclosure.

Figure 14:
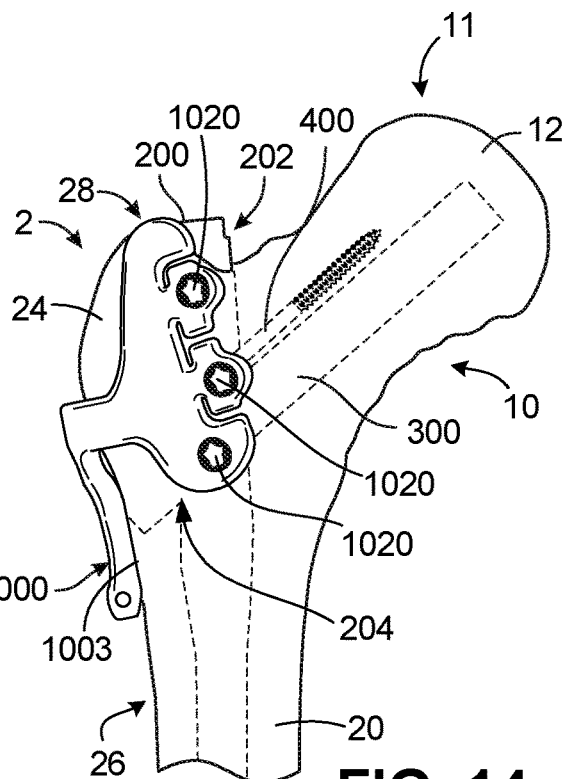
FIG. 14 shows a side view of the femoral fracture fixation device and the femur bone shown in FIGS. 12 and 13, illustrating certain components in phantom, in accordance with one example of the present disclosure.
Figure 13:
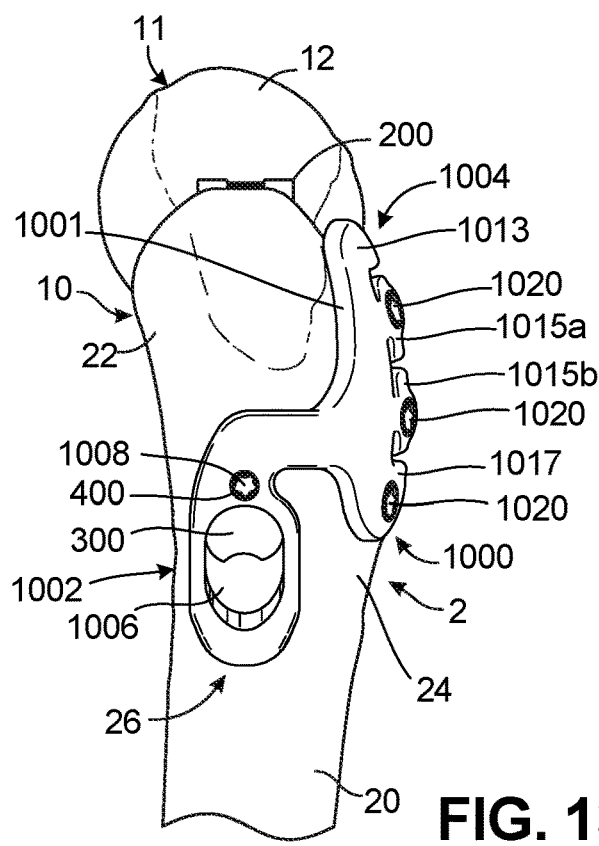
FIG. 13 shows a front view of the femoral fracture fixation device and the femur bone shown in FIG. 12, in accordance with one example of the present disclosure.

FIG. 12 shows a perspective view of a femoral fracture fixation device (or system) 2 operatively mounted to a femur bone, in one example of the present disclosure. FIG. 13 shows a front view of the femoral fracture fixation device 2 and a femur bone, in accordance with one example of the present disclosure. FIG. 14 shows a side view of the femoral fracture fixation device 2 and the femur bone, illustrating some components in phantom, in accordance with one example of the present disclosure. FIGS. 12-14 are discussed concurrently below.

The femoral fracture fixation device 2 can include an extramedullary plate 1000, an intramedullary nail 200, a bone fastener 300, and an anterior connecting fastener 400. The extramedullary plate 1000, as shown in FIGS. 12-14, can be consistent with FIGS. 10-11 above. Also shown in FIGS. 12-14 is a femur 10, which can include a femur head 12, a greater trochanter 16, a lesser trochanter 18, a femur shaft 20, a lateral surface 26, and a medullary cavity 28. The greater trochanter 16 can include an anterior surface 22 and a posterior surface 24. The intramedullary nail 200 and the bone fastener 300, can be consistent with the description of FIGS. 6-9 above.

In some cases, a femur, such as femur 10 can be fractured in one or more places proximate femoral head 12. This type of fracture can require a mechanical fixture, such as fracture fixation device 2, to stabilize femur 10 and promote healing. In some examples, the femoral fracture fixation device 2, or an alternative embodiment, can be inserted into a patient using a closed, intramedullary surgical technique that requires minimal exposure of the femur. In some examples, image intensification equipment can be employed to guide the surgeon during the procedure.

After preparing the surgical site, the medullary cavity 28 of the femur 10 can be reamed with an appropriate reaming tool to create or enlarge the medullary cavity 28 for insertion of the intramedullary nail 200. Progressively larger reaming tools can be inserted into a proximal end of the femur 10, and can be used to increase the diameter of the medullary cavity 28. In some examples, a guide pin or wire can be inserted into the cavity 28, and then the intramedullary nail 200 can be guided into the medullary cavity 28 of the femur 10.

Next, the extramedullary plate 1000 can be inserted into the opening such that the bone contacting surface 1003 interfaces with the lateral surface 26 of the femur 10 and the posterior support portion 1004 interfaces with the posterior side or surface 24 of the femur 10 in the region of the greater trochanter 16. The posterior support portion 1004 can be positioned to curve around the femur 10 and can flare out in width from the connection portion 1014 in the wing-shape shown, for example, and can be shaped and proportioned to fit against the posterior surface 24 of the region of the greater trochanter 16 (as in FIG. 12). In general, the extramedullary plate 1000 can be contoured to follow a general shape of the lateral surface 26 of the femur 10 near a proximal end 11 of the femur 10. The extramedullary plate 1000 can also be contoured to a surface of the femur 10 extending at least toward the posterior side 24 of the femur 10, near a region of the greater trochanter 16. It should be appreciated that in order for the extramedullary plate 1000 to be fitted across a range of bone sizes, shapes and types, the shapes and sizes can vary across a range of extramedullary plates.

In some examples, during positioning of the extramedullary plate 1000 the medial fingers 1015a and 1015b can be bent or flexed at joints 1022a and 1022b, respectively, such that the fingers 1015a and 1015b can move relative to each other and to the posterior support portion 1014 to align or interface with a portion of the posterior side 24 of femur 10, while tabs 1024a and 1024b can limit relative movement of medial fingers 1015a and 1015b. In some other examples, the proximal finger 1013 and the distal finger 1017 can also be bent and positioned.

Once the extramedullary plate 1000 is positioned, it can be attached to the femur 10. Any number of bone screws or fastening devices can be inserted through any of the openings in the extramedullary plate 1000 in order to sufficiently attach the extramedullary plate 1000 to the femur 10. Fasteners, such as those indicated by reference numeral 1020 in FIGS. 12-14, can extend through openings 1018 and can be used to affix the posterior support portion 1004 to the posterior side or surface 24 of the greater trochanter 16. A fastener 400 can also be affixed to the femur 10 at the lateral surface 26 through opening 1008 of main body portion 1002. This step can be performed either before or after bone fastener 300 is secured to femur 10.

After the intramedullary nail 200 is inserted and after the extramedullary plate 1000 is attached to the femur 10, the bone fastener 300 can be inserted by the bone fastener insertion assembly 500, for example. The bone fastener 300 (most visible in FIG. 14) can be inserted through opening 1006 of extramedullary plate 1000. An angle, shape, and configuration of the opening 1016 can allow the bone fastener 300 to be directed through the opening 1016 and into the femur 10 at a correct angle to allow the bone fastener 300 to be inserted through a corresponding proximal opening or bore 204 (see FIG. 14) in the intramedullary nail 200. The bone fastener 300 can then extend through the proximal opening 204 in the intramedullary nail 200 and into the femur head 12.

As described above with respect to extramedullary plate 100, in the description of FIGS. 8-9, a bone fastener insertion assembly 500 can used to secure bone fastener 300 to extramedullary plate 1000 and to femur 10.

Though FIGS. 12-14 show femoral fracture fixation device 2 mounted to a lateral and posterior portion of femur 10, it should be understood that femoral fracture fixation device 2 is shown mounted to/in the femur 10 by way of example and that the systems of this disclosure can be alternatively used for fixating or securing bone segments located at other anatomical regions without departing from the present disclosure.

Figure 15:
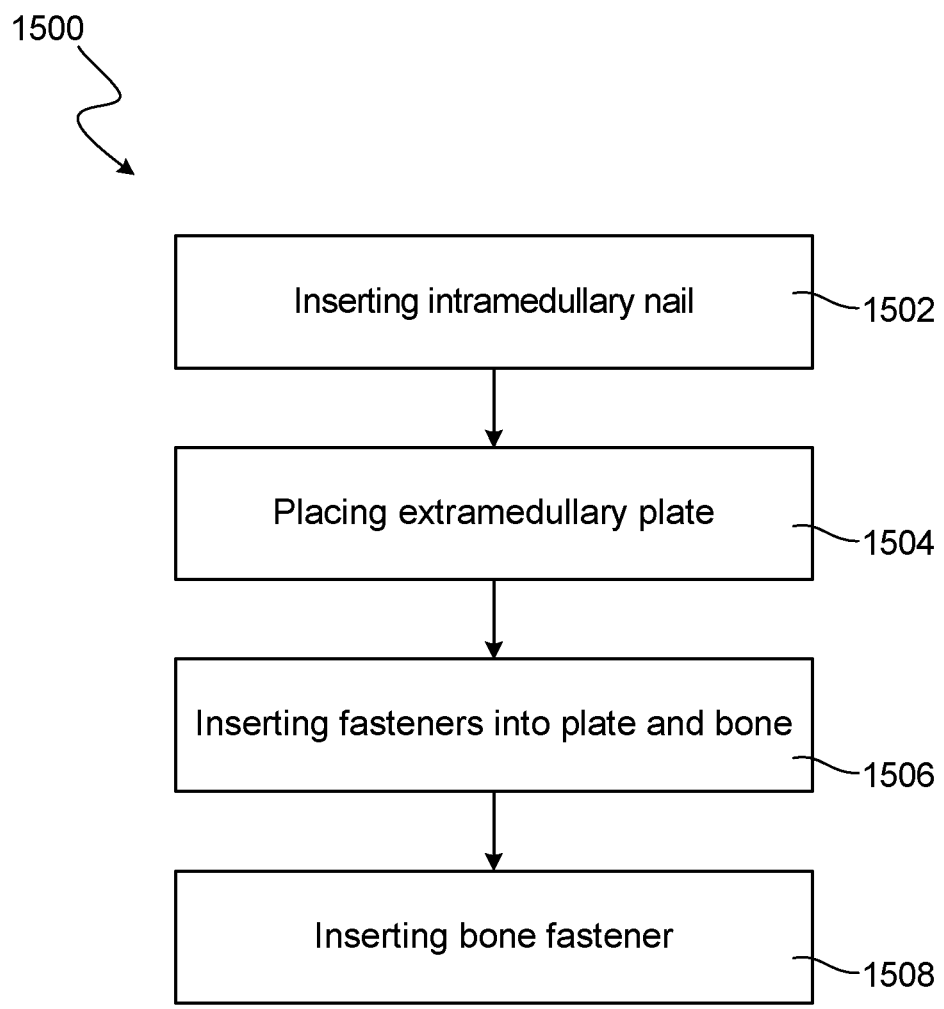
FIG. 15 shows a flow chart of a method, in accordance with one example of the present disclosure.

FIG. 15 shows a flow chart of method 1500, in accordance with one example of the present disclosure. The steps or operations of the method 1500 are illustrated in a particular order for convenience and clarity; many of the discussed operations can be performed in a different sequence or in parallel, and some operations may be excluded, without materially impacting other operations. The method 1500, as discussed, includes operations performed by multiple different actors, devices, and/or systems. It is understood that subsets of the operations discussed in the method 1500 attributable to a single actor, device, or system could be considered a separate standalone process or method.

In some examples, method 1500 can be a method of treating a fracture in a femur, where the femur includes a medullary cavity, a head portion, a shaft portion including a lateral surface, and a greater trochanter region including a posterior surface an anterior surface. In one example, method 1500 can begin at step 1502, where an intramedullary nail having an elongated shape and an opening adjacent a proximal end can be inserted into the medullary cavity. For example, intramedullary nail 200 can be inserted into the medullary cavity 28 of the femur 10.

At step 1504, an extramedullary plate, such as extramedullary plates 100 or 1000, can be placed adjacent the femur, where the extramedullary plate includes a main body portion configured for connection to the lateral surface of the femur shaft, and including a plurality of openings configured to receive a plurality of fasteners for attachment of the main body portion to the femur. The plate can further include a posterior support portion extending from the main body portion and can include a plurality of openings configured to receive a plurality of fasteners for attachment of the posterior support portion to the posterior surface of the greater trochanter region of the femur.

At step 1506, at least one of the plurality of fasteners can be inserted through one of the plurality of openings in the main body portion and the posterior support portion to attach the main body portion to the lateral surface of the femur shaft and to attach the posterior support portion to the posterior surface of the greater trochanter region of the femur.

At step 1508, a bone fastener having an elongated shape can be inserted through one of the plurality of openings of the main body portion of the extramedullary plate, through the opening of the intramedullary nail, and into the head portion of the femur.

In another example, the main body portion can include a flange that extends toward the anterior surface of the greater trochanter region of the femur after the extramedullary plate is attached to the femur, wherein the flange includes an opening that can accommodate an anterior connecting fastener configured to extend through the opening and to attach to the femur, and wherein the method further comprises a step of inserting the anterior connecting fastener through the opening of the flange and into the femur.

In another example, the extramedullary plate can further include a connection portion configured to attach the main body portion and the posterior support portion, which includes at least one opening that is configured to receive at least one fastener for attachment of the connection portion to the femur, and wherein the method further comprises a step of inserting the at least one fastener through the at least one opening of the connection portion.

In another example, further comprising a steps of attaching a bone fastener insertion tool to the extramedullary plate, and inserting the bone fastener into the femur through the tool.

In another example, one or more fingers of the posterior support portion can be bent to engage the posterior surface of the greater trochanter region of the femur. For example, during positioning of the extramedullary plate 1000 the medial fingers 1015a and 1015b can be bent or flexed at joints 1022a and 1022b, respectively, such that the fingers 1015a and 1015b can move relative to each other and to the posterior support portion 1014 to align or interface with a portion of the posterior side 24 of femur 10, while tabs 1024a and 1024b can limit relative movement of medial fingers 1015a and 1015b.

In another example, a bone contacting surface of the posterior support portion can be angled from a bone contacting surface of the main body portion in a range of about 10 to 230 degrees.

Figure 16A:
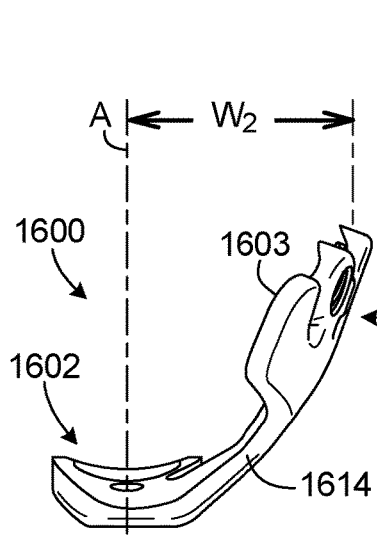
FIG. 16A shows a top view of an extramedullary plate, in accordance with one example of the present disclosure.
Figure 16B:
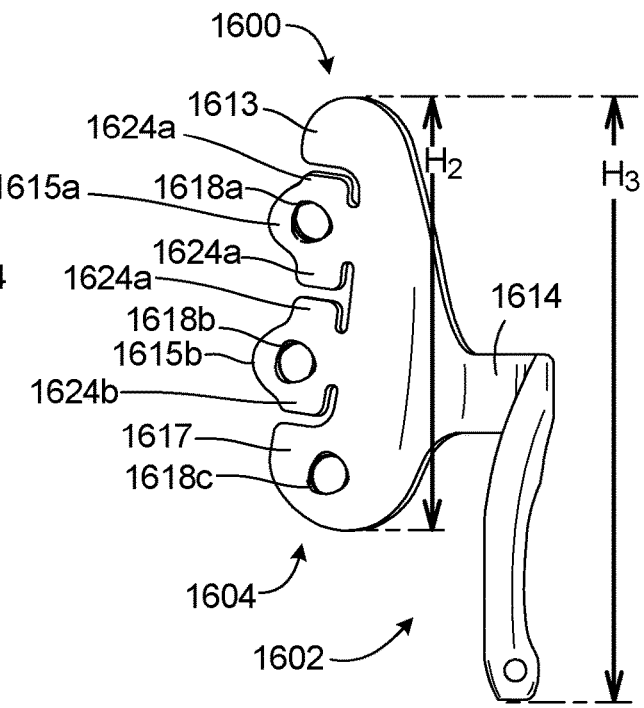
FIG. 16B shows a side view of an extramedullary plate, in accordance with one example of the present disclosure.
Figure 16C:
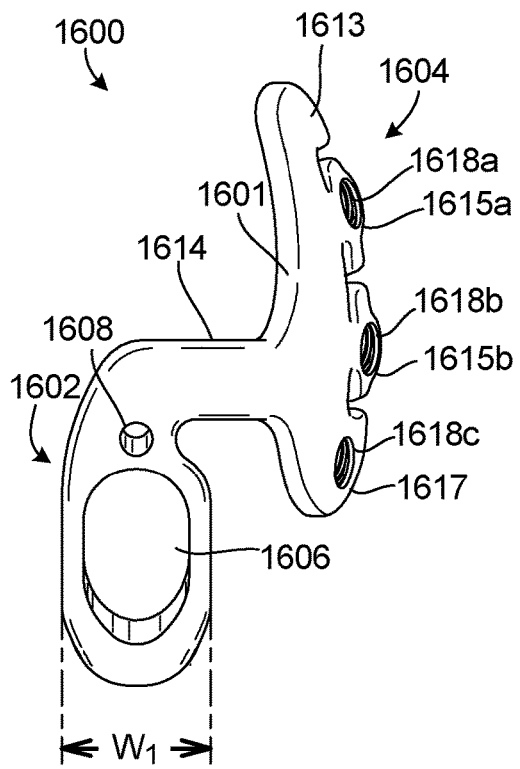
FIG. 16C shows a front view of an extramedullary plate, in accordance with one example of the present disclosure.
Figure 16D:
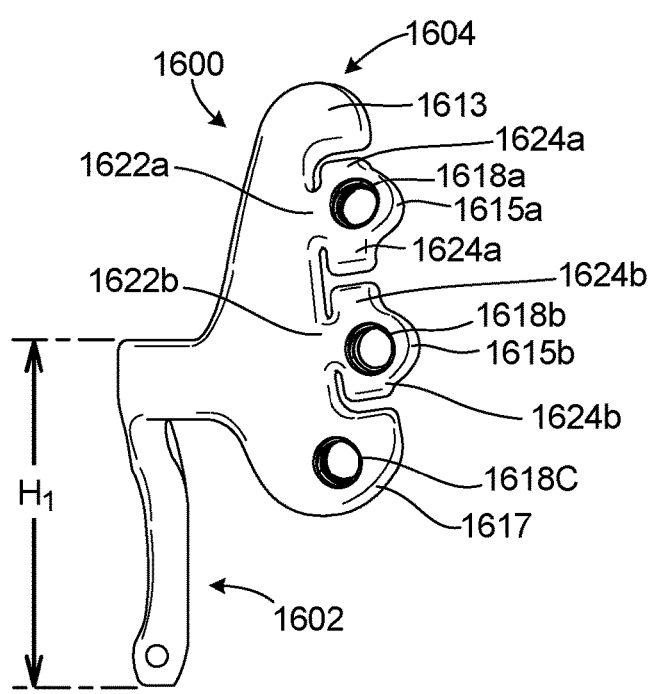
FIG. 16D shows a side view of an extramedullary plate, in accordance with one example of the present disclosure.

FIG. 16A shows a top view of an extramedullary plate 1600, in accordance with one example of the present disclosure. FIG. 16B shows a side view of the extramedullary plate 1600, in accordance with one example of the present disclosure. FIG. 16C shows a front view of the extramedullary plate 1600, in accordance with one example of the present disclosure. FIG. 16D shows a side view of the extramedullary plate 1600, in accordance with one example of the present disclosure. FIGS. 16A-16D are discussed below concurrently.

The extramedullary plate 1600 can include a main body portion 1602, a posterior support portion 1604, and a connecting portion 1614. The main body portion 1602 can include a bone contacting surface 1603 (only visible in FIG. 16B), a bone anchor opening 1006 (not visible in FIGS. 16B and 16D), and an opening 1608 (only visible in FIG. 16C). The posterior support portion 1604 can include a proximal finger 1613, medial fingers 1615a and 1615b, and a distal finger 1617. The medial fingers 1615a and 1615b can include medial openings 1618a and 1618b, respectively, and the distal finger 1617 can include distal opening 1618c.

The components of the extramedullary plate 1600 can be similar to the extramedullary plate 1000 discussed above, however, the extramedullary plate 1600 can be adapted to a particular size range. For example, the extramedullary plate 1600 can include a size W1 (shown in FIG. 16C), which can indicate a substantial medial-lateral width of main body portion 1602. In some examples, width W1 can be approximately 15 millimeters (mm). In other examples, the main body portion 1602 can have a width W1 of other sizes such as 1, 2, 3, 4, 5, 6, 7, 8, 9, 10, 11, 12, 13, 14, 16, 17, 18, 19, 20, 25, 30 mm and the like. The extramedullary plate 1600 can also have a width W2 corresponding to a medial-lateral width from axis A of the main body 1602 to a substantially outer-most portion of the posterior support portion 1604. In some examples, the width W2 can be 23 mm. In other examples, the width W2 can be other sizes such as 14, 15, 16, 17, 18, 19, 20, 21, 22, 24, 25, 26, 27, 28, 29, 30 mm and the like. In some examples, the widths W1 and W2 can be selected or optimized for fitment on the femur 10 of a patient.

Similarly, the extramedullary plate 1600 can include a size H1 (shown in FIG. 16D), which can indicate a substantially superior-inferior height of the main body portion 1602. The extramedullary plate 1600 can also include a size H2 (shown in FIG. 16B), which can indicate a substantially superior-inferior height of the posterior body portion 1604, where height H3 (shown in FIG. 16D) can indicate a substantially superior-inferior height of the extramedullary plate 1600. In some examples, H1 can be 35 mm, H2 can be 44 mm, and H3 can be 61 mm. However, each of heights H1-H3 can be other heights, such as 1-100 mm and the like. In some examples, the heights H1, H2, and H3 can be selected or optimized for fit on the femur 10 of a patient. By offering an extramedullary plate 1600 that can be selected for fit on femur 10 of a patient, patient comfort and healing can be improved, which can also help to reduce revisions.

FIG. 17A shows a top view of an extramedullary plate 1700, in accordance with one example of the present disclosure. FIG. 17B shows a side view of extramedullary the plate 1700, in accordance with one example of the present disclosure. FIG. 17C shows a front view of the extramedullary plate 1700, in accordance with one example of the present disclosure. FIG. 17D shows a side view of the extramedullary plate 1700, in accordance with one example of the present disclosure. FIGS. 17A-17D are discussed below concurrently.

The extramedullary plate 1700 can be similar to extramedullary plates 1000 and 1600 discussed above, except that the extramedullary plate 1700 can be relatively smaller. As discussed below in further detail, the size of various components of the extramedullary plate 1700 can be smaller than those of the extramedullary plates 1000 and/or 1600 to accommodate installation on a patient having a relatively smaller femur 10 and/or femoral head 12.

For example, the extramedullary plate 1700 can include a size W1 (shown in FIG. 17C), which can indicate a substantial medial-lateral width of main body portion 1702. In some examples, width W1 can be approximately 15 millimeters (mm). In other examples, the main body portion 1702 can have a width W1 of other sizes such as 1, 2, 3, 4, 5, 6, 7, 8, 9, 10, 11, 12, 13, 14, 16, 17, 18, 19, 20, 25, 30 mm and the like. The extramedullary plate 1700 can also have a width W2 corresponding to a medial-lateral width from axis A of the main body 1702 to a substantially outer-most portion of the posterior support portion 1704. In some examples, the width W2 can be 18 mm. In other examples, the width W2 can be other sizes such as 14, 15, 16, 17, 19, 20, 21, 22, 23, 24, 25, 26, 27, 28, 29, 30 mm and the like. In some examples, the widths W1 and W2 can be selected to be adapted to the femur 10 of a patient.

Similarly, the extramedullary plate 1700 can include a size H1 (shown in FIG. 17D), which can indicate a substantially superior-inferior height of the main body portion 1702. The extramedullary plate 1700 can also include a size H2 (shown in FIG. 17B), which can indicate a substantially superior-inferior height of the posterior body portion 1704, where height H3 (shown in FIG. 17D) can indicate a substantially superior-inferior height of the extramedullary plate 1700. In some examples, H1 can be 35 mm, H2 can be 38 mm, and H3 can be 53 mm. However, each of heights H1-H3 can be other heights, such as 1-100 mm and the like. In some examples, the heights H1, H2, and H3 can be selected for fit on the femur 10 of a patient. By providing an extramedullary plate 1700 that can be selected for fit on the femur 10 of a patient, fit of the extramedullary plate 1700 on the femur 10 can be improved, which can improve patient comfort and healing and can help to reduce revisions. As discussed below, the extramedullary plate 1700 can differ from the extramedullary plate 1600 in other ways.

In some examples, the medial fingers 1715a and 1715b can include tabs 1724a and 1724b, respectively, which can be substantially proximal and distal extensions from the fingers 1715a and 1715b towards adjacent fingers. The tabs 1724a and 1724b can be sized to control movement or deflection of fingers 1715a and 1715b relative to each other by causing contact when a maximum desired deflection is reached. The fingers and tabs of the extramedullary plate 1700 can be adjusted according to the size of the extramedullary plate 1700.

In one example, the proximal finger 1713, medial fingers 1715a and 1715b, and a distal finger 1717 can be relatively smaller than the proximal finger 1613, medial fingers 1615a and 1615b, and the distal finger 1617 of the extramedullary plate 1600 to accommodate the posterior support portion 1704 being smaller than the posterior support portion 1604. Accordingly, finger joints 1722a and 1722b (which can retain the medial fingers 1715a and 1715b) can be relatively smaller than finger joints 1622a and 1622b (which can retain the medial fingers 1615a and 1615b to accommodate smaller medial fingers 1715a and 1715b.

Additionally, the medial fingers 1715a and 1715b can include fewer tabs than the medial fingers 1615a and 1615b. For examples, the medial finger 1615a can include two tabs 1624a and the medial finger 1715a can include only one tab 1724a. Also, the medial finger 1615b can include two tabs 1624b and the medial finger 1715b can include only one tab 1724b. The reduced number of tabs of the medial fingers 1715 of the extramedullary plate 1700 can help to provide a similar range of flexibility or movement of the medial fingers 1715 as the medial fingers 1615 of extramedullary plate 1600. In some examples, tabs 1724a and 1724b can be adjacent to each other, as shown in FIG. 17D. However, in other examples, tab 1724a can be adjacent to proximal finger 1713 and/or tab 1724b can be adjacent to distal finger 1717.

In some other examples, the size of tabs 1724a and 1724b can also be selected based on a size of the medial fingers 1715 and/or the size of the posterior support portion 1704. The ability to select a size of the finger joints 1722a and 1722b, placement of the tabs 1724, number of the tabs 1724, and size of the tabs 1724 can provide the extramedullary plate 1700 the ability to accommodate various sizes of the posterior body portion 1704.

In some examples, the extramedullary plates 1600 and 1700, as well as the fasteners used therewith, can be formed of titanium, stainless steel, cobalt chrome, plastic—such as polyetheretherketone (PEEK), polyethylene, ultra high molecular weight polyethylene (UHMWPE), or a carbon composite-resorbable polylactic acid (PLA), polyglycolic acid (PGA), combinations or alloys of such materials or any other appropriate material that has sufficient strength to be secured to and hold bone, while also having sufficient biocompatibility to be implanted into a body. Although the above list of materials includes many typical materials out of which bone plates and bone screws are generally made, it should be understood that bone plates and bone screws or fasteners comprised of any appropriate, biocompatible material are within the scope of this disclosure.

Changes and modifications, additions and deletions may be made to the structures and methods recited above and shown in the drawings without departing from the scope or spirit of the invention and the following claims.

Additional Notes and Examples

To further illustrate devices, systems and methods disclosed herein, the following non-limiting examples are provided:

Example 1 is a femur fracture fixation device for treating a femur, the femur having a medullary cavity, a head portion, a shaft portion including a lateral surface, and a greater trochanter region including a posterior surface and an anterior surface, the femur fixation device comprising: an intramedullary nail having an elongated shape configured for insertion into the medullary cavity, and including an opening adjacent a proximal end; an extramedullary plate including: a main body portion configured for connection to the lateral surface of the femur shaft, and including a plurality of openings configured to receive a plurality of fasteners for attachment of the main body portion to the femur; and a posterior support portion extending from the main body portion and including a plurality of openings configured to receive a plurality of fasteners for attachment of the posterior support portion to the posterior surface of the greater trochanter region of the femur; and a bone fastener having an elongated shape configured for insertion through one of the plurality of openings of the main body portion of the extramedullary plate, through the opening of the intramedullary nail, and into the head portion of the femur.

In Example 2, the subject matter of Example 1 optionally includes wherein the main body portion includes a flange that extends toward the anterior surface of the greater trochanter region of the femur when the extramedullary plate is attached to the femur, and includes an opening that can accommodate an anterior connecting fastener configured to extend through the opening for attachment to the femur.

In Example 3, the subject matter of Example 2 optionally includes wherein the anterior connecting fastener comprises a bone screw.

In Example 4, the subject matter of any one or more of Examples 1-3 optionally include wherein the posterior support portion has a wing-shape.

In Example 5, the subject matter of any one or more of Examples 1-4 optionally include wherein the posterior support portion includes a plurality of struts located between the plurality of openings.

In Example 6, the subject matter of any one or more of Examples 1-5 optionally include wherein the extramedullary plate further comprises a connection portion configured to attach the main body portion and the posterior support portion, the connection portion including at least one opening that is configured to receive a fastener for attachment of the connection portion to the femur.

In Example 7, the subject matter of any one or more of Examples 1-6 optionally include wherein a bone contacting surface of the posterior support portion can be angled from a bone contacting surface of the main body portion in a range of about 10 to about 230 degrees.

Example 8 is a femoral fixation device for attachment to a femur, the femur having a medullary cavity, a head portion, a shaft portion including a lateral surface, and a greater trochanter region including a posterior surface and an anterior surface, the femoral fixation device comprising: a body portion couplable to the lateral surface of the femur shaft, the body portion including a bone anchor opening to receive a bone anchor therethrough; and a posterior support portion extending from the main body portion and comprising a finger extending from the plate, the finger engageable with a posterior surface of the greater trochanter region of the femur, and the finger including an opening configured to receive a fastener therethrough.

In Example 9, the subject matter of Example 8 optionally includes wherein the posterior support further comprises a proximal finger extending from the plate engageable with a posterior surface of the greater trochanter region of the femur proximate a proximal end of the femur.

In Example 10, the subject matter of any one or more of Examples 8-9 optionally include wherein the main body portion includes a second opening at the lateral surface of a proximal end of the femur configured to receive a lateral connecting fastener.

In Example 11, the subject matter of any one or more of Examples 8-10 optionally include wherein the posterior support portion has a wing-shape.

In Example 12, the subject matter of any one or more of Examples 8-11 optionally include wherein the finger cantilevers from the posterior portion to allow movement of the finger relative to the posterior portion.

In Example 13, the subject matter of any one or more of Examples 8-12 optionally include a second finger extending from the plate, the second finger engageable with a posterior surface of the greater trochanter region of the femur, and the second finger including an opening configured to receive a second fastener therethrough.

In Example 14, the subject matter of Example 13 optionally includes wherein the first and second fingers are spaced apart from each other to allow relative movement of the first and second fingers.

In Example 15, the subject matter of any one or more of Examples 8-14 optionally include wherein the posterior portion cantilevers from the body portion such that the posterior portion is moveable relative to the body portion.

Example 16 is a method of treating a fracture in a femur, the femur having a medullary cavity, a head portion, a shaft portion including a lateral surface, and a greater trochanter region including a posterior surface and an anterior surface, the method comprising: inserting an intramedullary nail having an elongated shape and an opening adjacent a proximal end into the medullary cavity; placing an extramedullary plate adjacent the femur, the extramedullary plate including: a main body portion configured for connection to the lateral surface of the femur shaft, and including a plurality of openings configured to receive a plurality of fasteners for attachment of the main body portion to the femur; and a posterior support portion extending from the main body portion and including a plurality of openings configured to receive a plurality of fasteners for attachment of the posterior support portion to the posterior surface of the greater trochanter region of the femur; inserting at least one of the plurality of fasteners through one of the plurality of openings in the main body portion and the posterior support portion in order to attach the main body portion to the lateral surface of the femur shaft and the posterior support portion to the posterior surface of the greater trochanter region of the femur; and inserting a bone fastener having an elongated shape through one of the plurality of openings of the main body portion of the extramedullary plate, through the opening of the intramedullary nail, and into the head portion of the femur.

In Example 17, the subject matter of Example 16 optionally includes wherein the main body portion includes a flange that extends toward the anterior surface of the greater trochanter region of the femur after the extramedullary plate is attached to the femur, wherein the flange includes an opening that can accommodate an anterior connecting fastener configured to extend through the opening and to attach to the femur, and wherein the method further comprises a step of inserting the anterior connecting fastener through the opening of the flange and into the femur.

In Example 18, the subject matter of any one or more of Examples 16-17 optionally include wherein the extramedullary plate further comprises a connection portion configured to attach the main body portion and the posterior support portion, which includes at least one opening that is configured to receive at least one fastener for attachment of the connection portion to the femur, and wherein the method further comprises a step of inserting the at least one fastener through the at least one opening of the connection portion.

In Example 19, the subject matter of any one or more of Examples 16-18 optionally include attaching a bone fastener insertion tool to the extramedullary plate, and inserting the bone fastener into the femur through the tool.

In Example 20, the subject matter of any one or more of Examples 16-19 optionally include bending one or more fingers of the posterior support portion to engage the posterior surface of the greater trochanter region of the femur.

Example 21 is a system for treating a fractured femur, the femur having a medullary cavity, a head portion, a shaft portion including a lateral surface, and a greater trochanter region including a posterior surface and an anterior surface, the system comprising: a femur fixation device comprising: an intramedullary nail having an elongated shape configured for insertion into the medullary cavity, and including an opening adjacent a proximal end; an extramedullary plate including: a main body portion configured for connection to the lateral surface of the femur shaft, and including a plurality of openings configured to receive a plurality of fasteners for attachment of the main body portion to the femur; and a posterior support portion extending from the main body portion and including a plurality of openings configured to receive a plurality of fasteners for attachment of the posterior support portion to the posterior surface of the greater trochanter region of the femur; a bone fastener having an elongated shape configured for insertion through one of the plurality of openings of the main body portion of the extramedullary plate, through the opening of the intramedullary nail, and into the head portion of the femur; and a bone fastener insertion tool configured to couple to the extramedullary plate and to insert the bone fastener into the femur.

Example 22 includes the system for treating a fractured femur of example 21, wherein the bone fastener insertion tool comprises a coupling sheath configured to couple the assembly to the extramedullary plate, and a bone fastener sheath configured to guide insertion of the bone fastener through the extramedullary plate and into the femur.

Example 23 includes the system of treating a fractured femur of any one of examples 21-22, wherein the main body portion includes a flange that extends toward the anterior surface of the greater trochanter region of the femur when the extramedullary pate is attached to the femur, and includes an opening that can accommodate an anterior connecting fastener configured to extend through the opening and to attach to the femur.

Example 24 includes the system of treating a fractured femur of example 10, wherein the anterior connecting fastener comprises a bone screw.

Example 25 includes the system of treating a fractured femur of any one of examples 21-24, wherein the posterior support portion has a wing-shape.

Example 26 includes the system of treating a fractured femur of any one of examples 21-25, wherein the posterior support portion includes a plurality of struts located between the plurality of openings.

Example 27 includes the system of treating a fractured femur of any one of examples 21-26, wherein the extramedullary plate further comprises a connection portion configured to attach the main body portion and the posterior support portion, which includes at least one opening that is configured to receive a fastener for attachment of the connection portion to the femur.

Example 28 includes the system of treating a fractured femur of any one of examples 21-27, wherein a bone contacting surface of the posterior support portion can be angled from a bone contacting surface of the main body portion in a range of about 10 to about 230 degrees.

In Example 29, the system, assembly, or method of any one of or any combination of Examples 1-29 is optionally configured such that all elements or options recited are available to use or select from.

The above Detailed Description includes references to the accompanying drawings, which form a part of the Detailed Description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the Detailed Description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The invention claimed is:

1. A femur fracture fixation device for treating a femur, the femur having a medullary cavity, a head portion, a shaft portion including a lateral surface, and a greater trochanter region including a posterior surface and an anterior surface, the femur fixation device comprising:
   an intramedullary nail having an elongated shape configured for insertion into the medullary cavity; and including an opening adjacent a proximal end;
   an extramedullary plate including:
      a main body portion configured for connection to the lateral surface of the femur shaft, and including a plurality of openings configured to receive a plurality of fasteners for attachment of the main body portion to the femur; and
      a posterior support portion extending from the main body portion and including a plurality of openings configured to receive a plurality of fasteners for attachment of the posterior support portion to the posterior surface of the greater trochanter region of the femur; and
   a bone fastener having an elongated shape configured for insertion through one of the plurality of openings of the main body portion of the extramedullary plate, through the opening of the intramedullary nail, and into the head portion of the femur.

2. The femur fracture fixation device of claim 1, wherein the main body portion includes a flange that extends toward the anterior surface of the greater trochanter region of the femur when the extramedullary plate is attached to the femur, and includes an opening that can accommodate an anterior connecting fastener configured to extend through the opening for attachment to the femur.

3. The femur fracture fixation device of claim 2, wherein the anterior connecting fastener comprises a bone screw.

4. The femur fracture fixation device of claim 1, wherein the posterior support portion has a wing-shape.

5. The femur fracture fixation device of claim 1, wherein the posterior support portion includes a plurality of struts located between the plurality of openings.

6. The femur fracture fixation device of claim 1, wherein the extramedullary plate further comprises a connection portion configured to attach the main body portion and the posterior support portion, the connection portion including at least one opening that is configured to receive a fastener for attachment of the connection portion to the femur.

7. The femur fracture fixation device of claim 1, wherein a bone contacting surface of the posterior support portion is angled from a bone contacting surface of the main body portion in a range of about 10 to about 230 degrees.

8. A method of treating a fracture in a femur, the femur having a medullary cavity, a head portion, a shaft portion including a lateral surface, and a greater trochanter region including a posterior surface and an anterior surface, the method comprising:
   inserting an intramedullary nail having an elongated shape and an opening adjacent a proximal end into the medullary cavity;
   placing an extramedullary plate adjacent the femur, the extramedullary plate including:
      a main body portion configured for connection to the lateral surface of the femur shaft, and including a plurality of openings configured to receive a plurality of fasteners for attachment of the main body portion to the femur; and
      a posterior support portion extending from the main body portion and including a plurality of openings configured to receive a plurality of fasteners for attachment of the posterior support portion to the posterior surface of the greater trochanter region of the femur;
   inserting at least one of the plurality of fasteners through one of the plurality of openings in the main body portion and the posterior support portion in order to attach the main body portion to the lateral surface of the femur shaft and the posterior support portion to the posterior surface of the greater trochanter region of the femur; and
   inserting a bone fastener having an elongated shape through one of the plurality of openings of the main body portion of the extramedullary plate, through the opening of the intramedullary nail, and into the head portion of the femur.

9. The method of claim 8, wherein the main body portion includes a flange that extends toward the anterior surface of the greater trochanter region of the femur after the extramedullary plate is attached to the femur, wherein the flange includes an opening that can accommodate an anterior connecting fastener configured to extend through the opening and to attach to the femur, and wherein the method further comprises a step of inserting the anterior connecting fastener through the opening of the flange and into the femur.

10. The method of claim 8, wherein the extramedullary plate further comprises a connection portion configured to attach the main body portion and the posterior support portion, which includes at least one opening that is configured to receive at least one fastener for attachment of the connection portion to the femur, and wherein the method further comprises a step of inserting the at least one fastener through the at least one opening of the connection portion.

11. The method of claim 8, further comprising:
   attaching a bone fastener insertion tool to the extramedullary plate, and inserting the bone fastener into the femur through the tool.

12. The method of claim 8, further comprising:
   bending one or more fingers of the posterior support portion to engage the posterior surface of the greater trochanter region of the femur.

* * * * *